(12) United States Patent
Watson et al.

(10) Patent No.: US 7,009,073 B2
(45) Date of Patent: Mar. 7, 2006

(54) METHOD FOR PREPARING INDAN-1,3-DICARBOXYLIC ACID

(75) Inventors: Timothy J. N. Watson, Waterford, CT (US); Mark Christopher Guzman, San Diego, CA (US); Patrice Arpin, Sorel-Tracy (CA)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 10/706,694

(22) Filed: Nov. 12, 2003

(65) Prior Publication Data

US 2005/0240057 A1    Oct. 27, 2005

Related U.S. Application Data

(60) Provisional application No. 60/427,981, filed on Nov. 20, 2002.

(51) Int. Cl.
*C07C 63/46* (2006.01)

(52) U.S. Cl. .................................................... 562/488
(58) Field of Classification Search .................... None
See application file for complete search history.

(56) References Cited

U.S. PATENT DOCUMENTS 6,410,550 B1   6/2002   Coe et al. .................. 514/289
6,410,551 B1   1/2003   Miller ........................ 717/114

OTHER PUBLICATIONS

Paul H. Mazzocchi, et al.; Synthesis and Pharmacological Activity of 2,3,4,5-Tetrahydro-1,5-methano-1H-3-benzazepines; J. Med. Chem., vol. 22, No. 4; p. 455-457 (1979).

*Primary Examiner*—Paul A. Zucker
(74) *Attorney, Agent, or Firm*—Steve T. Zelson; A. David Joran

(57) ABSTRACT

A method for preparing indan-1,3-dicarboxylic acid compounds which are useful intermediates in the syntheses of aryl fused azapolycyclic compounds as agents for the treatment of neurological and psychological disorders.

10 Claims, No Drawings

METHOD FOR PREPARING INDAN-1,3-DICARBOXYLIC ACID

BACKGROUND OF THE INVENTION

The present invention is directed to a method for preparing indan-1,3-dicarboxylic acid and derivatives thereof which are useful intermediates in the synthesis of aryl fused azapolycyclic compounds. U.S. patent application Ser. No. 09/514002 filed Feb. 25, 2000 discloses the synthesis of selected intermediates which are useful in the preparation of aryl fused azapolycyclic compounds.

The synthesis, composition, and methods of use of certain aryl fused azapolycyclic compounds which exhibit activity as agents for the treatment of neurological and psychological disorders is disclosed in U.S. Pat. No. 6,410,550 B1. The foregoing patent application and patent are incorporated by reference herein in their entirety.

SUMMARY OF THE INVENTION

The present invention provides a process for preparing a compound of the formula

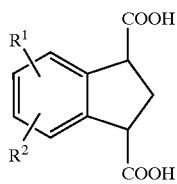

wherein $R^1$ arid $R^2$ are independently selected from hydrogen, $C_1$–$C_5$ alkyl $C_1$–$C_5$ alkoxy, trifluoromethyl, halogen, sulfonyl alkyl, alkylamino, amide, ester, aryl-alkyl, heteroalkyl, and arylalkoxy. The compounds of formula I are prepared by the acid or base catalyzed hydrolysis of a compound having the formula

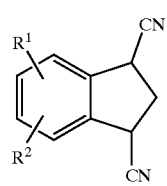

wherein $R^1$ and $R^2$ are selected independently from hydrogen, $C_1$–$C_5$ alkyl, $C_1$–$C_5$ alkoxy, trifluoromethyl, halogen, sulfonyl alkyl, alkylamino, amide, ester, aryl-alkyl, heteroalkyl, and arylalkoxy.

Compounds of the formula II may be prepared by the hydrogenation of a compound of formula

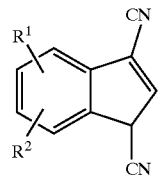

in the presence of a suitable hydrogenation catalyst, wherein $R^1$ and $R^2$ are as defined above.

Compounds of formula III may be prepared by the reaction of a compound of formula

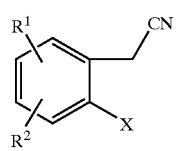

with 3-ethoxyacrylonitrile, of formula

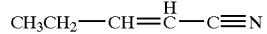

in the presence of palladium II acetate, tricyclohexylphosphine and a base in a water miscible solvent. $R^1$ and $R^2$ are as defined above and X is selected from the group consisting of chlorine, bromine, and iodine.

The hydrolysis of the indan II to the corresponding dicarboxylic acid is conducted in the presence of either an acid catalyst or a base catalyst. The acid catalyst is comprised of either a single acid or a mixture of acids. Suitable acids are glacial acetic acid, concentrated hydrochloric acid and sulfuric acid.

Preferably the catalyst is a mixture of glacial acetic acid and concentrated hydrochloric acid. The hydrolysis is carried out at a temperature in the range of about 25° C. to about 100° C. for a period of about 1 hour to about 20 hours.

Preferably the temperature is about 100° C. for a period of about 2 hours.

Under basic hydrolysis, the conditions of time and temperature are about the same as for acid hydrolysis. Suitable base catalysts include Group I metal alkoxides, sodium hydroxide, lithium hydroxide, and potassium hydroxide.

Generally, the hydrolysis reaction will include a suitable amount of water as is well known to those skilled in the art.

The hydrogenation of compound III may be conducted at a hydrogen pressure of about 14 psi to about 50 psi. Preferably the pressure is about 40 psi. Suitable hydrogenation catalysts include palladium on carbon, platinum on carbon, and Raney nickel. A preferred catalyst is 5% palladium on carbon.

The synthesis of a compound of formula III is carried out by first condensing a compound of formula IV with 3-ethoxyacrylonitrile followed by ring closure, in situ, by the application of heat. The reaction is carried out in the presence of palladium II acetate, tricyclohexyl phosphine, a base, and a water miscible solvent.

In a preferred embodiment the compound of formula I is indan-1,3-dicarboxylic acid.

DETAILED DESCRIPTION OF THE INVENTION

The present invention provides a method for preparing indan-1,3-diacarboxylic acid and its derivatives according to Scheme 1. In the first step of the process, a compound of formula IV is condensed with 3-ethoxyacrylonitrile in the presence of palladium II acetate, tricyclohexylphosphine, and a base in a water miscible solvent. Initially, the intermediate dinitrile of formula IVa is formed, but not isolated. With the application of heat, the dinitrile of formula IVa is cyclized to a compound of formula III. The resulting indene dinitrile (III) is next hydrogenated to the corresponding indan compound II. Hydrolysis of a compound of formula II in the presence of an aqueous acid or base catalyst results in the formation of the dicarboxylic acid of formula I.

Scheme I

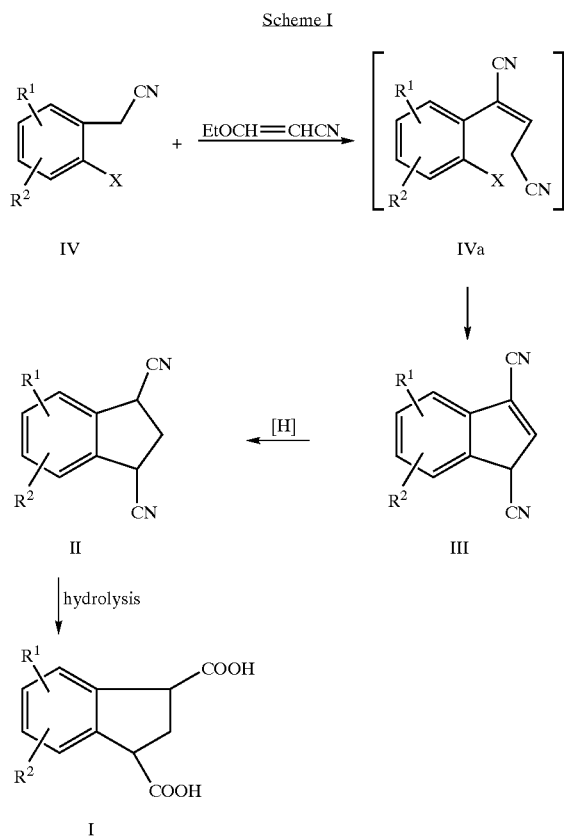

wherein $R^1$ and $R^2$ are selected independently from hydrogen, $C_1$–$C_5$ alkyl, $C_1$–$C_5$ alkoxy, trifluoromethyl, halogen, sulfonyl alkyl, alkylamino, amide, ester, aryl-alkyl, heteroalkyl, and arylalkoxy The dicarboxylic acids of the present invention are useful intermediates in the synthesis of certain aryl fused azapolycyclic compounds of the formula

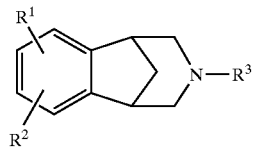

wherein $R^1$ and $R^2$ are selected independently from hydrogen, $C_1$–$C_5$ alkyl, $C_1$–$C_5$ alkoxy, trifluoromethyl, halogen, sulfonyl alkyl, alkylamino, amido, ester, aryl-alkyl, heteroalkyl, and arylalkoxy and wherein $R^3$ is $C_1$–$C_6$ alkyl. This is disclosed in U.S. Pat. No. 6,410,551 B1, which is incorporated herein by reference.

The indan-1,3-dicarboxylic acids disclosed herein are useful intermediates in the preparation of compounds of formula V, according to the reaction steps outlined in Scheme 2. The proposed process which provides an alternate path to compounds of formula V, is based upon a reaction sequence reported by Mazzocchi, P. H., J. Med. Chem. Vol. 22, no. 4, 455 (1979).

Scheme 2

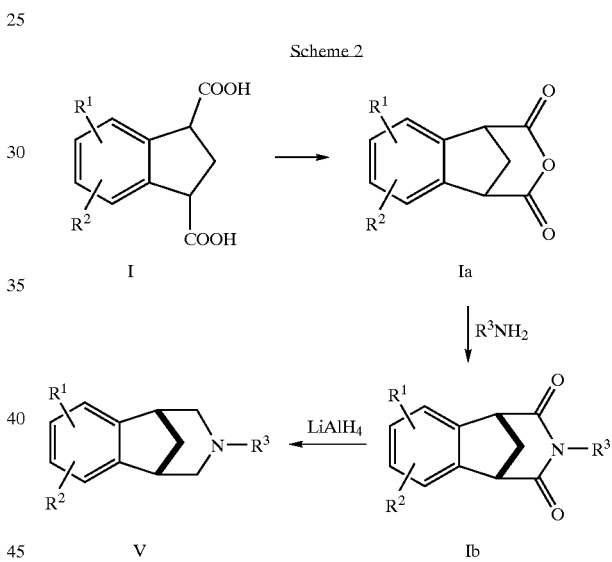

Referring to Scheme 2, the dicarboxylic acid having the formula I is cyclized to the corresponding anhydride by treatment with acetic anhydride at 100° C. The anhydride having formula II is converted to the cyclic imide III in concentrated $NH_4OH$. Next the imide III is reduced with lithium aluminium hydride to the cyclic amine of formula V.

Examples of specific compounds of the formula V are the following compounds:
  4-ethynyl-5-chloro-10-aza-tricyclo[6.3.0$^{2,7}$]dodeca-2(7), 3,5-triene;
  3-trifluoromethyl-10-aza-tricyclo[6.3.0$^{2,7}$]dodeca-2(7),3, 5-triene;
  4,5-bistrifluoromethyl-10-aza-tricyclo[6.3.1.0$^{2,7}$]dodeca-2(7),3,5-triene;
  4-choro-5-trifluoromethyl-10-aza-tricyclo[6.3.1.0$^{2,7}$]dodeca-2(7),3,5-triene;
  4-amino-10-aza-tricyclo[6.3.1.0$^{2,7}$]dodeca-2(7),3,5-triene;
  4-nitro-10-aza-tricyclo[6.3.0$^{2,7}$]dodeca-2(7),3,5-triene;
  4-methyl-10-aza-tricyclo[6.3.0$^{2,7}$]dodeca-2(7),3,5-triene;

4-fluoro-10-aza-tricyclo[6.3.0$^{2,7}$]dodeca-2(7),3,5-triene;

4-trifluoromethyl-10-aza-tricyclo[6.3.0$^{2,7}$]dodeca-2(7),3,5-triene;

4,5-difluoro-10-aza-tricyclo[6.3.0$^{2,7}$]dodeca-2(7),3,5-triene; and pharmaceutically acceptable salts thereof.

Compounds of formula V bind to neuronal nicotinic acetylcholine specific receptor sites and are useful in modulating cholinergic function. Such compounds are useful in the treatment of inflammatory bowel disease (including but not limited to ulcerative colitis, pyoderma gangrenosum and Crohn's disease), irritable bowel syndrome, spastic dystonia, chronic pain, acute pain, celiac sprue, pouchitis, vasoconstriction, anxiety, panic disorder, depression, bipolar disorder, autism, sleep disorders, jet lag, amyotrophic lateral sclerosis (ALS), cognitive dysfunction, hypertension, bulimia, anorexia, obesity, cardiac arrythmias, gastric acid hypersecretion, ulcers, pheochromocytoma, progressive supranuclear palsy, chemical dependencies and addictions (e.g., dependencies on, or addictions to nicotine (and/or tobacco products), alcohol, benzodiazepines, barbiturates, opioids or cocaine), headache, migraine, stroke, traumatic brain injury (TBI), obsessive-compulsive disorder (OCD), psychosis, Huntington's chorea, tardive dyskinesia, hyperkinesia, dyslexia, schizophrenia, multi-infarct dementia, age-related cognitive decline, epilepsy, including petit mal absence epilepsy, senile dementia of the Alzheimer's type (AD), Parkinson's disease (PD), attention deficit hyperactivity disorder (ADHD) and Tourette's Syndrome.

The compounds of the formula V and their pharmaceutically acceptable salts (hereafter "the active compounds") can be administered via either the oral, transdermal (e.g., through the use of a patch), intranasal, sublingual, rectal, parenteral or topical routes. Transdermal and oral administration are preferred. These compounds are, most desirably, administered in dosages ranging from about 0.01 mg up to about 1500 mg per day, preferably from about 0.1 to about 300 mg per day in single or divided doses, although variations will necessarily occur depending upon the weight and condition of the subject being treated and the particular route of administration chosen. However, a dosage level that is in the range of about 0.001 mg to about 10 mg per kg of body weight per day is most desirably employed. Variations may nevertheless occur depending upon the weight and condition of the persons being treated and their individual responses to said medicament, as well as on the type of pharmaceutical formulation chosen and the time period and interval during which such administration is carried out. In some instances, dosage levels below the lower limit of the aforesaid range may be more than adequate, while in other cases still larger doses may be employed without causing any harmful side effects, provided that such larger doses are first divided into several small doses for administration throughout the day.

The active compounds can be administered alone or in combination with pharmaceutically acceptable carriers or diluents by any of the several routes previously indicated. More particularly, the active compounds can be administered in a wide variety of different dosage forms, e.g., they may be combined with various pharmaceutically acceptable inert carriers in the form of tablets, capsules, transdermal patches, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents. In addition, oral pharmaceutical compositions can be suitably sweetened and/or flavored. In general, the active compounds are present in such dosage forms at concentration levels ranging from about 5.0% to about 70% by weight.

For oral administration, tablets may contain a variety of excipients, disintegrants, lubricating agents, and fillers. Aqueous suspensions for oral administration may be combined with flavor, coloring matter, and diluents.

For parental administration, a solution of the active compound may be suitably buffered and may be diluted with a vegetable oil or propylene glycol.

The following examples are provided for the purpose of further illustration and are not intended to limit the scope of the claimed invention.

EXAMPLE 1

Inden-1,3-dicarbonitrile

In a flame dried three-necked flask, added palladium II acetate (0.175 g, 0.78 mmol) and tricyclohexylphosphine (0.328 g, 1.17 mmol). Purged with nitrogen for half a hour, then added 20 ml of anhydrous THF and stirred for an additional 30 minutes. Cooled down to 0° C., then added slowly sodium tert-butoxide (9.41 g, 96.5 mmol) and stirred for 1 hour at 0° C. Filled the adding funnel with a solution of 2-bromobenzenecyanide (5.06 ml, 39 mmol), 3-ethoxy acrylonitrile (4.01 ml, 30 mmol) and 5 ml of anhydrous THF. Added very slowly dropwise the solution into the palladium solution. Stirred at room temperature for 30 minutes.

Heated up the solution in all oil bath up 70° C. When the solution reach the 45° C., an exothermic reaction occurred. Waited until the ebullition stopped. Continued heating to 70° C. The reaction was complete within 30 minutes. Cooled down to room temperature.

Added 75 ml of water and 75 ml of $CH_2Cl_2$. Separated the organic layer and washed the aqueous one with an additional 25 ml of $CH_2 Cl_2$. With an aqueous solution of HCl 5M, lowered the pH of the aqueous layer to 1. Extracted the aqueous layer with 4×30 ml of EtOAc and washed the combined extraction with brine. Dried with MgSO4, filtered through Cellite and concentrated under reduced pressure to give a brown solid (13.8 g). Recrystallized from MeOH to give a beige white powder (7.062 g, 54.5%).

Anal. Calcd for $C_{11}H_6N_2$: C, 79.44; H, 3.61; N, 16.85. Found C, 79.41; 3.61, N, 16.60

$^1$H NMR spectra analysis

| Chem. Shift ppm | Multiplicity | Coupling constant Hz | Integration | Assignation |
|---|---|---|---|---|
| 12.96 | singlet | — | 1 | e, e' |
| 7.35 | multiplet | — | 2 | b, b' |
| 7.23 | singlet | — | 1 | g |
| 6.87 | multiplet | — | 2 | a, a' |

EXAMPLE 2

Indan-1,3-dicarbonitrile

In a parr bottle containing Pd/C (10% wt), added 1 (5.00 g, 30.08 mmol) and 200 ml of EtOAc. Purged with N2 and H2 and hydrogenated under a $H_2$ pressure of 40 psi at RT. Within 2 hours, the reaction was complete. The solution was filtered trough Cellite and concentrated under reduced pressure to gave a brown solid (5.63 g, 111.2%). Recrystallized in MeOH to give a white pink solid (2.56 g, 50.59%). The filtrated was concentrated under reduced pressure and the brown solid was recrystallized again to give a pink white solid (0.576 g, 11.38% for overall of 61.97%)

Anal Calcd for C11H8N2: C, 78.55; H, 4.79; N 16.66. Found C, 78.55; H, 4.55; N, 16.37.

$^1$H NMR spectra analysis

| Chem. Shift ppm | Multiplicity | Coupling constant Hz | Integration | Assignation |
|---|---|---|---|---|
| 7.49 | multiplet | — | 2 | b, b' |
| 7.43 | multiplet | — | 2 | a, a' |
| 4.58 | triplet | 8.089 | 2 | e, e' |
| 2.99 | doublet of triplets | 12.857 8.502 | 2 | g |

EXAMPLE 3

Indan-1,3-dicarboxylic acid

In a round bottom flask, added 2 (1.50 g, 9.03 mmol) with glacial acetic acid (7.5 ml) and concentrated hydrochloric acid (7.5 ml). Heated to 100C. After 2 hours, the reaction was cooled down to room temperature and diluted with 50 ml of water. The aqueous layer was extracted with EtOAc (30, 2×20 ml). Extracted the organic layer with a saturated bicarbonate solution (5×30 ml). Lowered the pH to 1 with HCl 5M and extracted with EtOAc (30, 2×20 ml). Washed with brine, dried and concentrated under reduced pressure to give a yellow solid (1.23 g, 66.1%). Suspened the yellow solid (1.23 g) in 50 ml of hot xylene (98° C.) for 2 hours. Cooled down to 0° C., filtered and washed with hexane to give a white yellow solid (1.03 g, 55.3%).

Anal calcd for $C_{11}H_6O_4$: C, 65.03; H, 3.47; N, 0.0. Found C, 6386; H, 4.69; N, 0.37

$^1$H NMR spectra analysis

| Chem. Shift ppm | Multiplicity | Coupling constant Hz | Integration | Assignation |
|---|---|---|---|---|
| 7.42 | multiplet | — | 2 | b, b' |
| 7.25 | multiplet | — | 2 | a, a' |
| 4.18 | triplet | 7.051 | 2 | e, e' |
| 4.11 | triplet | 8.089 | | |
| 4.04 | triplet | 8.502 | | |
| 2.70 | triplet | 8.502 | 2 | g |

We claim:
1. A process for the preparation of compounds having the formula

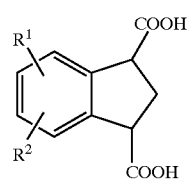

I wherein $R^1$ and $R^2$ are selected independently from hydrogen, $C_1$–$C_5$ alkyl, $C_1$–$C_5$ alkoxy, trifluoromethyl, halogen, sulfonyl alkyl, alkylamino, amide, ester, aryl-alkyl, heteroalkyl, and arylalkoxy comprising hydrolyzing a compound of formula

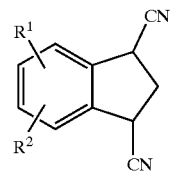

II in the presence of an acid or base catalyst
wherein $R^1$ and $R^2$ are selected independently from hydrogen, $C_1$–$C_5$ alkyl, $C_1$–$C_5$ alkoxy, trifluoromethyl, halogen, sulfonyl alkyl, alkylamino, amide, ester, aryl-alkyl, heteroalkyl, and arylalkoxy.

2. The process according to claim 1 wherein said catalyst is an acid catalyst comprising a mixture of glacial acetic acid and concentrated hydrochloric acid.

3. The process according to claim 1 wherein said compound is indan-1,3-dicarboxylic acid.

4. The process according to claim 1 wherein said compound of formula II is prepared by reacting a compound of the formula

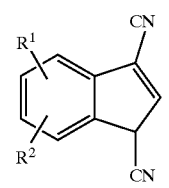

III with hydrogen in the presence of a hydrogenation catalyst, wherein $R^1$ and $R^2$ are independently selected from hydrogen and $C_1$–$C_6$ alkyl, trifluoromethyl, halogen, sulfonyl alkyl, alkylamino, amide, ester, aryl-alkyl, heteroalkyl, and arylalkoxy.

5. The process according to claim 4, wherein said hydrogenation catalyst is palladium on carbon.

6. The process of claim 4 wherein a compound of formula III is prepared by reacting a compound of the formula

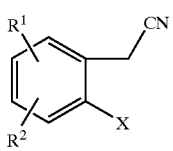

IV with 3-ethoxyacrylonitrile in the presence of a catalyst comprising tricyclohexylphosphine, palladium II acetate, and a base in a water miscible organic solvent,
wherein $R^1$ and $R^2$ are independently selected from hydrogen, $C_1$–$C_5$ alkyl, $C_1$–$C_5$ alkoxy, trifluoromethyl, halogen, sulfonyl alkyl, alkylamino, amide, ester, aryl-alkyl, heteroalkyl, and arylalkoxy and X selected from the group consisting of chlorine, bromine, or iodine.

7. The process according to claim 6 wherein said base is sodium t-butoxide.

8. The process according to claim 6 wherein said water miscible solvent is tetrahydrofuran.

9. The process according to claim 5, wherein said hydrogenation catalyst is 5% palladium on carbon.

10. The process according to claim 1, wherein said catalyst is a base catalyst selected from the group consisting of Group I metal alkoxides, sodium hydroxide, lithium hydroxide, and potassium hydroxide.

* * * * *